United States Patent [19]
Miura et al.

[11] Patent Number: 5,258,719
[45] Date of Patent: Nov. 2, 1993

[54] CAPACITIVE COAGULATION DETECTING DEVICE FOR MIXED PHASE CONTAINER

[75] Inventors: Yasuhiro Miura, Chiba; Yutaka Shiomi, Ichihara, both of Japan

[73] Assignee: Sumitomo Chemical Co., Ltd., Osaka, Japan

[21] Appl. No.: 894,569

[22] Filed: Jun. 5, 1992

[30] Foreign Application Priority Data

Jul. 6, 1991 [JP] Japan .................. 3-136805

[51] Int. Cl.$^5$ .................. G01R 27/26; G01N 27/22
[52] U.S. Cl. .................. 324/673; 324/663; 324/686; 324/690
[58] Field of Search ........... 324/658, 663, 673, 680, 324/686, 687, 688, 690, 71.1

[56] References Cited

U.S. PATENT DOCUMENTS

| | | | |
|---|---|---|---|
| 3,233,173 | 2/1966 | Lees et al. | 324/663 |
| 3,663,955 | 5/1972 | Shimizu | 324/658 |
| 4,371,977 | 2/1983 | Jenkins, III et al. | 378/51 |
| 4,710,757 | 12/1987 | Haase | 324/663 X |
| 4,899,101 | 2/1990 | Porges | 324/663 |

FOREIGN PATENT DOCUMENTS

| | | |
|---|---|---|
| 62-28961 | 6/1987 | Japan . |
| 02-31148 | 2/1990 | Japan ............... 324/658 |

*Primary Examiner*—Gerard R. Strecker
*Assistant Examiner*—Diep Do
*Attorney, Agent, or Firm*—Birch, Stewart, Kolasch & Birch

[57] ABSTRACT

A device for detecting a coagulation in a mixed phase container, such as a fluidized bed type olefin polymerization reactor, includes at least one coagulation detecting part mounted on an inner surface of the reactor, and a coagulation detecting circuit for outputting an electrical signal in response to a change in capacitance between a main electrode of the coagulation detecting part and the surrounding inner surface of the reactor. When any coagulation is attached on the inner surface of the mixed phase container, the state of production of the coagulation can be obtained from a change in output signal from the coagulation detecting circuit connected to the coagulation detecting part.

14 Claims, 15 Drawing Sheets

CAPACITIVE COAGULATION DETECTING DEVICE FOR MIXED PHASE CONTAINER

BACKGROUND OF THE INVENTION

The present invention relates to a mixed phase container, e.g., a fluidized bed type olefin polymerization reactor and, more particularly, is concerned with a device for detecting coagulations or chunks produced in the mixed phase container.

When a mixed phase container, e.g., a fluidized bed type olefin polymerization reactor, is used for a long period of time, coagulations are produced in the container and may be attached on the inner surface of the side wall of the container. Various techniques have been devised heretofore to detect such a coagulation. One known technique is to utilize radiation, as described in, e.g., U.S. patent application Ser. No. 160,288, filed on Jun. 12, 1980 by John Mitchell Jenkins, 3rd, et al, now U.S. Pat. No. 4,371,977.

According to this technique, a radiation source is arranged at the center of the container, and a plurality of radiation detectors are arranged around the container. When a change in density of the mixed phase between the radiation source and the detectors is detected, the presence and size of a coagulation can be recognized. In this technique, it is possible to use a radiation source having a considerably high-level radiation of about 1,000 mCi.

Generally, a mixed phase container, e.g., a fluidized bed type olefin polymerization reactor is huge and of substantially cylindrical shape, which has a diameter of several meters and a height of ten to twenty meters. When the container is clogged, it is usual that an operator enters the container to remove the clogging object. Also, the operator enters the container to perform periodic inspections. Accordingly, if a radiation source is arranged in the reactor, very strict consideration must be paid to ensure the safety of the operator in the container. Also, a high-level technique is needed to ensure safety against earthquake or fire. In view of these respects, the conventional technique using the radiation as described above is not practical.

In addition, the size of the smallest detectable coagulation is limited in this technique using radiation. Therefore, a need exists to improve the capability for detecting smaller coagulations to prevent clogging in the container more reliably.

In order to resolve these problems, simple means of using an observation glass window which is mounted on the side wall of the container was suggested. In fact, however, it is difficult to visually observe coagulations through the observation glass window because the field of view is interfered with by the substance in the mixed phase container.

SUMMARY OF THE INVENTION

It is, therefore, an object of the present invention to provide a device which can safely detect any coagulation in a mixed phase container.

It is another object of the present invention to provide a device which can detect a very small coagulation in a mixed phase container.

It is still another object of the present invention to provide a device which can detect any coagulation in a product discharge pipe of a mixed phase container.

According to an aspect of the present invention, a coagulation detecting device for detecting a coagulation in a mixed phase container, such as a fluidized bed type olefin polymerization reactor, includes at least one coagulation detecting part having a first electrode and a second electrode, and a coagulation detecting circuit for outputting an electrical signal in response to a change in capacitance between the first and second electrodes.

The coagulation detecting circuit includes a bridge circuit having two AC power supplies, and a capacitor consisting of the first and second electrodes of the coagulation detecting part is added to one arm of the bridge circuit as an impedance factor to be monitored.

In a preferred embodiment, the second electrode of the coagulation detecting part is a portion of the inner wall surface of the mixed phase container, the wall surface portion positioned near the first electrode of the coagulation detecting part.

When any coagulation is produced and attached on the inner wall surface of the mixed phase container, since the density of the coagulation is larger than that of the mixed phase, the capacitance between the first and second electrode of the coagulation detecting part changes. Accordingly, the state of production of the coagulation can be obtained from a change in output signal from the coagulation detecting circuit connected to the coagulation detecting part.

Also, according to another aspect of the present invention, a coagulation detecting device for detecting a coagulation in a mixed phase container includes at least one vibration sensor mounted on a product discharge pipe extending from the mixed phase container, and means for counting the number of coagulations passing through the product discharge pipe on the basis of a signal output from the vibration sensor.

When coagulations start to be discharged to the product discharge pipe, the coagulations impinge against the discharge pipe to produce vibration noise. Such noise is not produced when no coagulation is present. Accordingly, when an output from the vibration sensor is analyzed, the number of coagulations passing through the discharge pipe can be detected. Furthermore, the state of production of the coagulation in the mixed phase container can be estimated from the number of coagulations.

These and other features and advantages of the present invention will become apparent to those skilled in the art upon a reading of the following detailed description when taken in conjunction with the drawings wherein there is shown and described an illustrative embodiment of the invention.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

BRIEF DESCRIPTION OF THE DRAWINGS

In the course of the following detailed description, reference will be made to the attached drawings in which.

DETAILED DESCRIPTION OF THE PREFERRED EMBODIMENT

Figure 1:
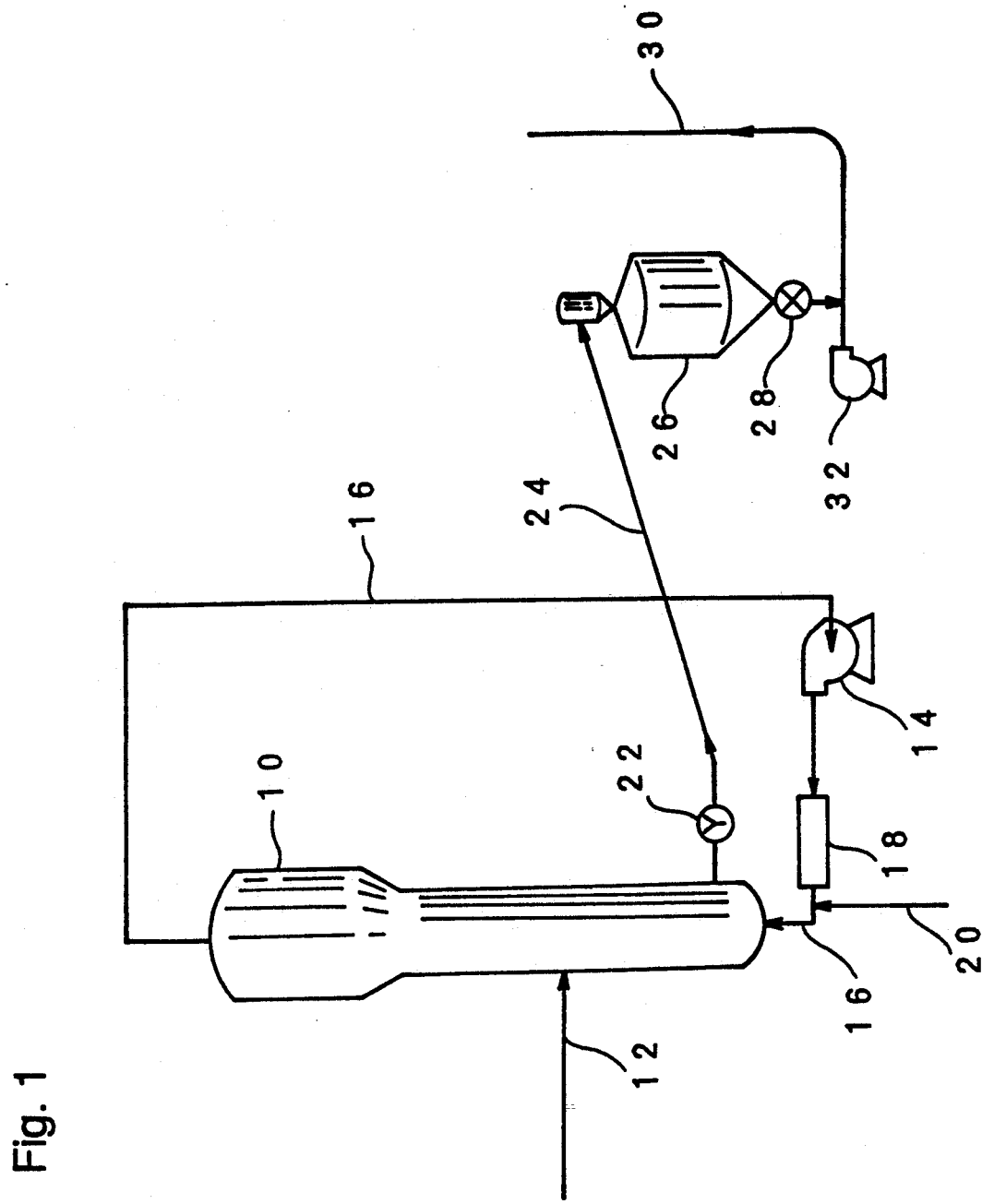
FIG. 1 is a view showing a fluidized bed type olefin polymerization reactor to which the present invention can be applied, and its peripheral piping systems.

FIG. 1 is a view showing a fluidized bed type olefin polymerization reactor 10, to which the present invention can be applied, and its peripheral piping systems. A mixed phase of a gas and a powder is formed and fluidized in the olefin polymerization reactor 10, and a polymerization reaction is continued in this state. The pressure in the olefin polymerization reactor 10 is about 10 to 30 kg/cm²G, and the temperature in it is about 70° to 100° C.

A catalyst and an olefin gas are supplied to the fluidized bed type olefin polymerization reactor 10 through an inlet port 12. This olefin gas is used mainly to transport the catalyst.

The olefin gas in the reactor 10 is constantly circulated by a circulation gas blower 14 through a gas line 16. A heat exchanger 18 connected midway along the gas line 16 serves to adjust the temperature of the circulation gas. The olefin gas is supplied through a line 20 in accordance with the progress step of the polymerization reaction.

A product produced by the polymerization reaction is supplied to a primary silo 26 through a discharge valve 22 and a discharge line 24 to be stored in it temporarily. The product is then fed onto a pneumatic line 30 by a rotary valve 28 and then sent to a desired place by the wind force of a pneumatic blower 32.

Coagulation detecting devices are provided on a side wall and in an interior of the fluidized bed type olefin polymerization reactor 10, and at a bent portion of the pneumatic line 30, respectively. The respective coagulation detecting devices will be described.

Figure 2:
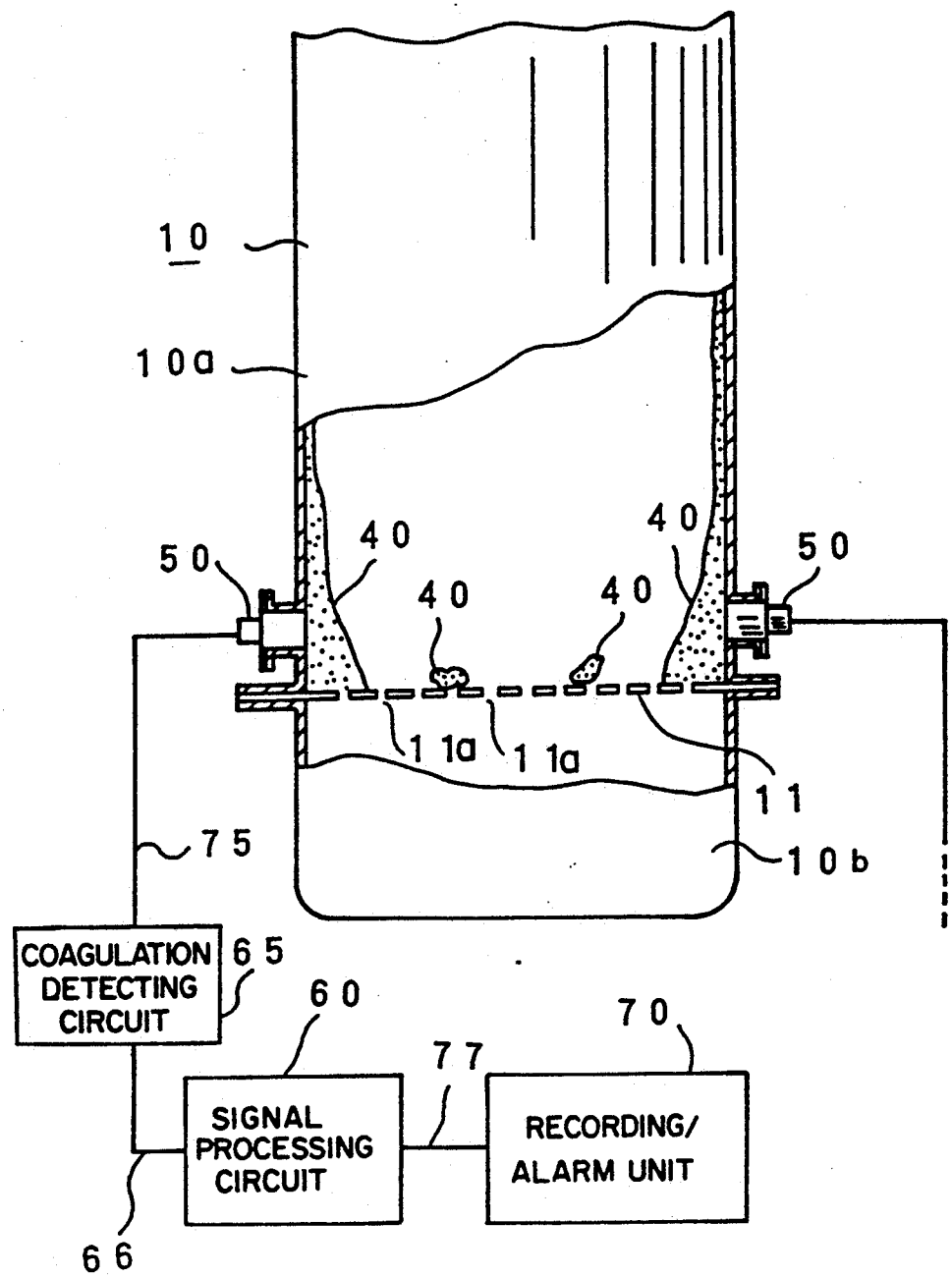
FIG. 2 is a partial enlarged view of the fluidized bed type olefin polymerization reactor.

FIG. 2 is a partial enlarged view of the fluidized bed type olefin polymerization reactor 10, with part of which being cut away to indicate the internal structure thereof. The olefin polymerization reactor 10 includes a cylindrical shell 10a and a bottom head 10b mounted on the lower end of the shell 10a. A dispersion plate 11 is interposed between the shell 10a and the bottom head 10b.

The circulation gas fed from the lower portion of the olefin polymerization reactor 10 is blown upward from a multiple of openings 11a formed in the dispersion plate 11 so that a mixed phase of the gas and powder is formed in the shell 10a of the reactor 10. The polymerization reaction of the mixed phase is continued in the mixed phase. During the process of the polymerization reaction, coagulations 40 are undesirably produced due to a change in state of the mixed phase or the other factors. Although the production process of the coagulations 40 is not completely clarified yet, it is clear that when the reaction is stopped to observe the interior of the olefin polymerization reactor 10, the coagulations 40 are present on the inner wall surface of the reactor 10 and the dispersion plate 11.

The coagulation detecting device according to the present invention as shown in FIG. 2 has coagulation detecting parts 50 for detecting the coagulation 40 formed on the inner wall surface of the shell 10a of the reactor 10. Each of the coagulation detecting parts 50 is used together with a coagulation detecting circuit 65, signal processing circuit 60 and a recording and/or alarming unit 70. An end section of each coagulation detecting part 50 is exposed inside from the inner wall surface of the reactor 10. The end section of the coagulation detecting part 50 cooperates with the inner wall surface in the vicinity of the end section to make a capacitor. The capacitance in the vicinity of the coagulation detecting part 50 is changed according to the presence of a coagulation. As a result, the presence of the coagulation 40 can be recognized from the change of capacitance.

This will be described in more detail. When reaction is caused in a condition that the pressure in the fluidized bed type olefin polymerization reactor 10 is about 10 to 30 kg/cm²G and the temperature is about 70° to 100° C., the density of the mixed phase is about 0.30 to 0.45 g/cm³. The density of the coagulation is about 0.70 to 0.80 g/cm³, which is about twice that of the mixed phase. There are following equations between the density and the dielectric constant, and between the dielectric constant and the capacitance, respectively:

$$\epsilon = \epsilon_s (\rho/\rho_s) \quad (1)$$

$$\epsilon = C/C_o \quad (2)$$

where:
- $\epsilon$ is the dielectric constant of the mixed phase;
- $\epsilon_s$ is the dielectric constant of the coagulation;
- $\rho$ is the density of the mixed phase;
- $\rho_s$ is the density of the coagulation;
- $C$ is the capacitance of the mixed phase; and
- $C_o$ is the capacitance of electrodes in outer air.

It is apparent from equations (1) and (2) that a change in density of the mixed phase can be regarded as a change in capacitance. Accordingly, a coagulation attached on the inner wall surface of the fluidized bed type olefin polymerization reactor 10 can be monitored from the change in the capacitance between the coagulation detecting part 50 and the inner wall surface of the reactor 10. Note that $\epsilon_s$ in equation (1) is about 2.3.

The coagulation detecting part 50 is connected to the coagulation detecting circuit 65 through a cable 75, and the change in the capacitance between the coagulation detecting part 50 and the inner wall surface of the reactor 10 is converted into the change in voltage by the coagulation detecting circuit 65. An output signal of the coagulation detecting circuit 65 is transmitted to a signal processing circuit 60 through a cable 66 and the output signal is properly processed and converted into a current signal of 4–20 mA. The current signal is then transmitted to the recording and/or alarming unit 70 through a cable 77 and monitored.

Figure 3:
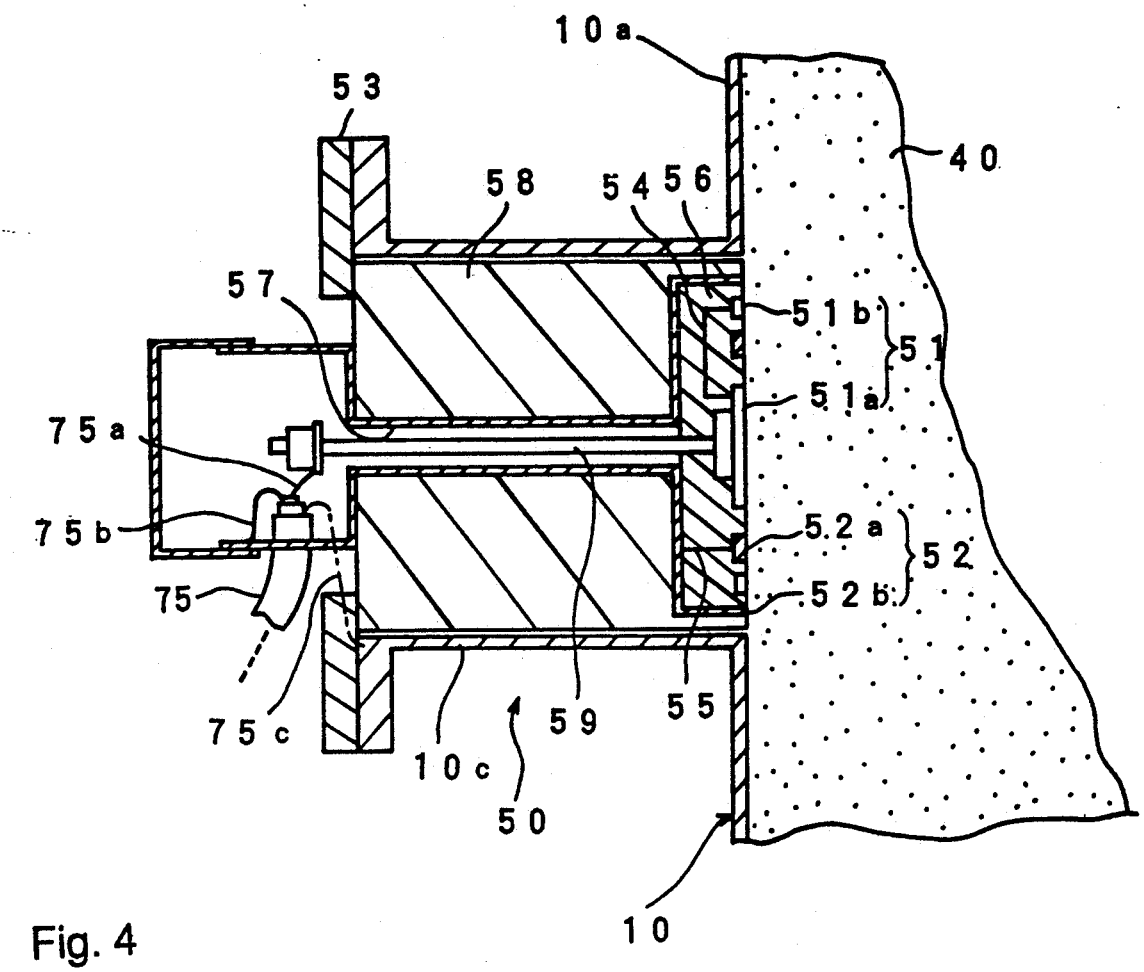
FIG. 3 is a sectional view of a coagulation detecting part mounted on the reactor of FIG. 2.
Figure 4:
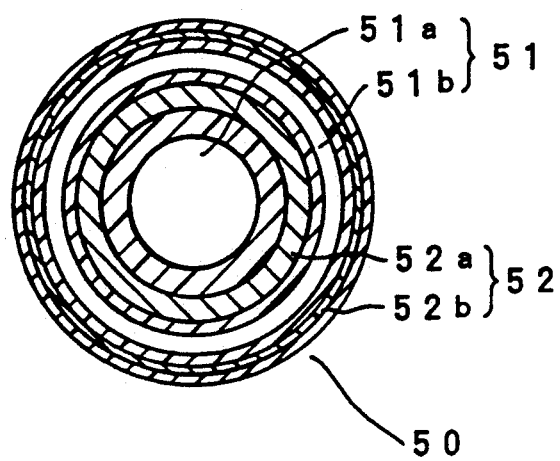
FIG. 4 is an end face view of the coagulation detecting part of FIG. 3, FIG. 5 schematically shows the arrangement of a coagulation detecting circuit connected to the coagulation detecting part of FIGS. 3 and 4.

FIGS. 3 and 4 show an example of the structure of the coagulation detecting part 50, in which FIG. 3 is a sectional view of the part 50 taken along its axis, and FIG. 4 is an end face view of the part 50 seen from the inside of the fluidized bed type olefin polymerization reactor 10. The coagulation detecting part 50 has a substantially cylindrical shape, and has a first electrode functioning as a main electrode 51 arranged on one end face thereof. The main electrode 51 is constituted by a disk-like electrode plate 51a and an annular electrode plate 51b. The electrode plate 51a is coaxially surrounded by the annular electrode plate 51b, and spaced from the electrode plate 51b. The two electrode plates 51a and 51b are electrically connected to each other by a connection wire 54.

Also, an annular electrode plate 52a is disposed between the electrode plates 51a and 51b, and an annular electrode plate 52b is disposed outside the electrode plate 51b. These electrode plates 52a and 52b constitutes a sub-electrode 52. The electrode plates 52a and 52b are electrically connected to each other by a connection wire 55. These electrodes 51 and 52 are embedded in insulating materials 56 and 58, e.g., tetrafluoric resin or ceramics.

A conductive pipe 57 extending through the insulating material 58 is connected to the sub-electrode plate 52b. A conductive rod 59 is coaxially disposed in the conductive pipe 57 so as not to contact the conductive pipe 57. One end of the conductive rod 59 is connected to the disk-like electrode plate 51a. The other end of the conductive rod 59 is connected to a core wire 75a of the cable 75. This cable 75 is a dual coaxial cable. An inner shielding wire of the cable 75 is connected to the conductive pipe 57 through a connecting wire 75b. An outer shielding wire is connected to a cylindrical body 10c through a connecting wire 75c (as shown in the phantom line in FIG. 3), the cylindrical body 10c provided on the lower portion of the shell 10a of the reactor 10.

Such a coagulation detecting part 50 is mounted on the reactor 10 by inserting it in the cylindrical body 10c and fixing a mounting flange 53 of the part 50 on the flange of the cylindrical body 10c. The characteristic feature of the coagulation detecting part 50 resides in that, since the main electrode 51 and the sub-electrode 52 have disk-like or annular shapes, it can have a wide detection area as required.

The coagulation detecting part 50 can detect a change in thickness of the coagulation 40 attached between the main electrode 51 and the inner wall surface (acting as the second electrode of the coagulation detecting part) of the grounded reactor 10 as a change in the capacitance. The sub-electrode 52 serves to enlarge the detection range. The operation of the sub-electrode 52 will become apparent upon a reading of the following description in reference to FIG. 5.

Figure 5:
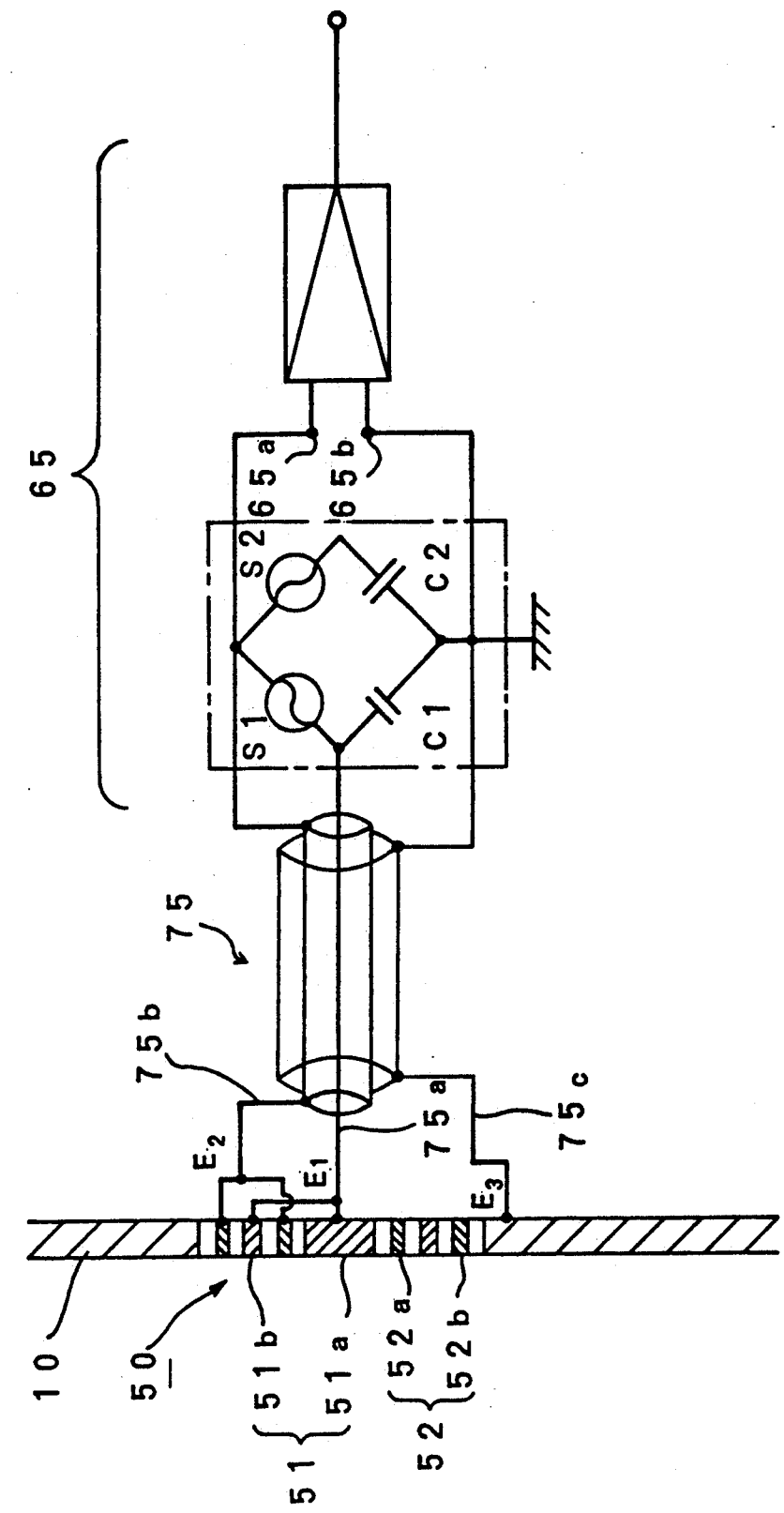

FIG. 5 schematically shows the arrangement of the coagulation detecting circuit 65 connected to the coagulation detecting part 50. This circuit 65 has a bridge circuit consisting of AC power supplies or synchronized high-frequency power supplies S1 and S2 and capacitors C1 and C2. The main electrode 51 is connected to the capacitor C1 and the power supply S1 via the core wire 75a of the dual coaxial cable 75. The other terminal of the capacitor C1 is grounded. The other terminal of the power supply S1 is connected to the sub-electrode 52 through an inner shielding wire of the coaxial cable 75 and the connecting wire 75b. The inner wall surface of the olefin polymerization reactor 10 is connected to a junction point between the capacitor C1 and C2 through the outer shielding wire of the coaxial cable 75 and a connecting wire 75c.

This bridge circuit is kept to be balanced and is adjusted so that difference of potential between a terminal 65a and a terminal 65b is kept to be a predetermined value. When any coagulation approaches the coagulation detecting part 50 or attaches to the coagulation detecting part 50 in the manner that the capacitance between the main electrode 51 and the inner wall surface of the reactor 10 changes, the balance in the transformer bridge circuit is broken so that high frequency signal caused by the high frequency power source appears between the terminal 65a and the terminal 65b. In this time, an average voltage of the high frequency signal which appears between the terminal 65a and the terminal 65b, changes in response to the change in the capacitance between the main electrode 51 and the inner wall surface of the reactor By the way, the density of electric line of force formed between the main electrode 51 and the inner wall surface of the reactor 10 near the coagulation detecting part 50 is remarkably high at an area where the main electrode 51 remarkably approaches the inner wall surface of the reactor 10. Therefore, even when a small coagulation which would not be needed to be detected approaches this area or attaches to the inner wall surface or the coagulation detecting part 50 near this area (herein after so called as a high density area of an electric line of force), the capacitance between the main electrode 51 and the inner wall surface of the reactor 10 changes remarkably so that an output to be detected is generated between the terminal 65a and the terminal 65b.

So, in order to prevent such an error detection, the sub-electrode 52 is provided in the coagulation detecting part 50 of this embodiment. The sub-electrode 52 is located near the high density area of an electric line of force between the main electrode 51 and the inner wall surface of the reactor 10 and connected to a junction between two high frequency power sources S1 and S2 of the coagulation detecting circuit 65. When an coagulation approaches the high density area of an electric line of force or attaches to the inner wall surface or the coagulation detecting part 50 near the high density area of an electric line of force the capacitance between the main electrode 51 and the sub-electrode 52 changes at the same time. This change functions so as to overcome an unbalance of the transformer bridge circuit caused by the change in the capacitance between the main electrode 51 and the inner wall surface of the reactor 10. Therefore, the above error detection can be prevented.

Figure 6:
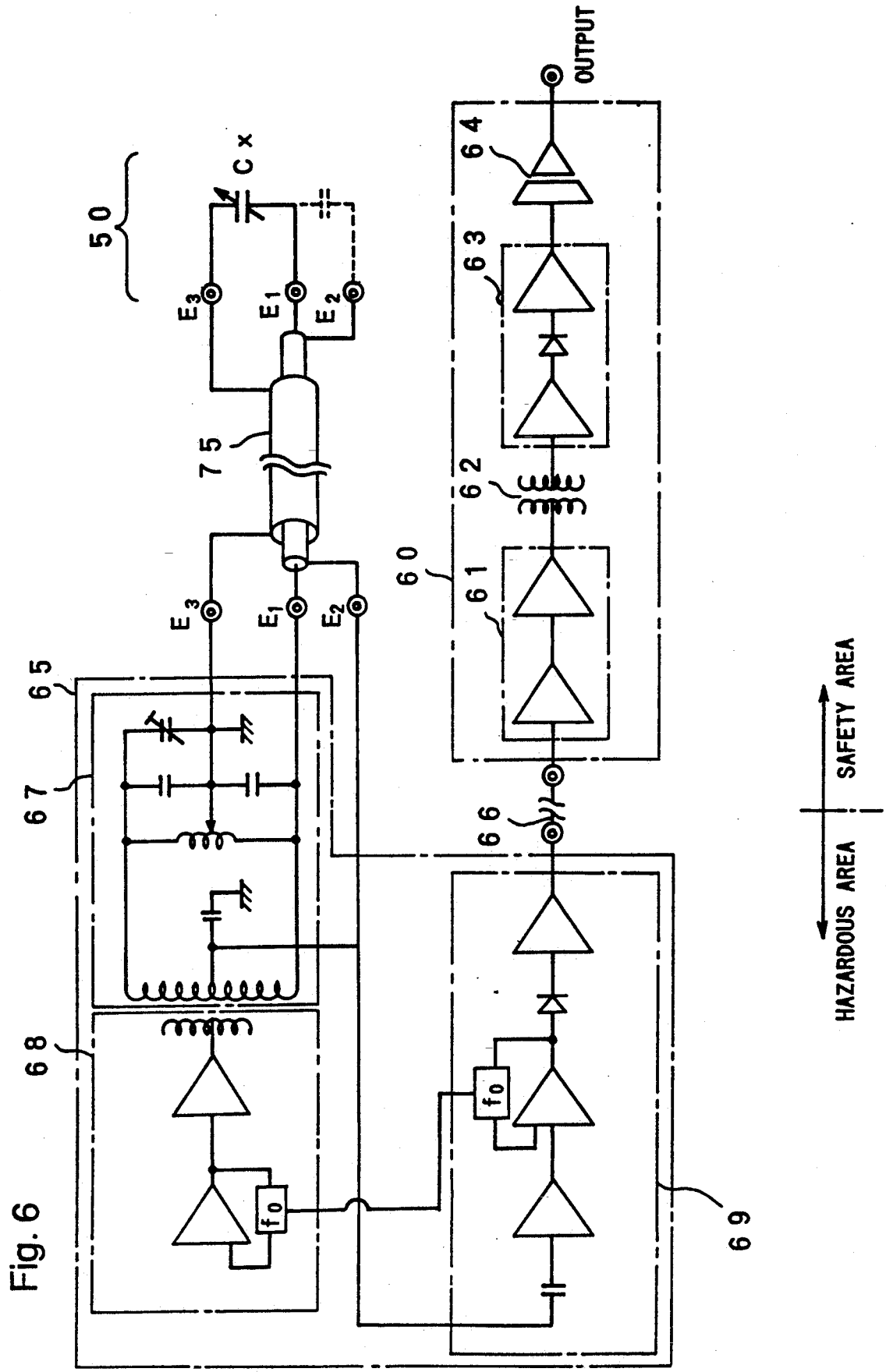
FIG. 6 shows a more concrete embodiment of the coagulation detecting circuit of FIG. 5 and further shows a concrete embodiment of a next signal processing circuit.

FIG. 6 shows a more concrete embodiment of the coagulation detecting circuit 65 shown in FIG. 5 and further shows a concrete embodiment of a next signal processing circuit 60. The coagulation detecting circuit 65 comprises a transformer bridge circuit 67, a high frequency oscillator 68 functioning as a high frequency power source for the bridge circuit 67 and a detector 69 for synchronistically detecting an output signal of the bridge circuit 67 with an oscillation frequency of the high frequency oscillator 68. The coagulation detecting circuit 65 is positioned relatively near the coagulation detecting part 50. An output terminal is connected to an input terminal of the signal processing circuit 60 which is positioned in a safety area. The signal processing circuit 60 converts the input signal into an AC signal in a circuit 61 and thereafter convert an AC signal into a direct current in a circuit 63 through a voltage converter 62. The converted direct current is converted into a current of 4–20 mA again by the voltage/current converter 64. The reason why the voltage converter 62 is provided on the way of the transmission, is to separate the power sources in the input and output circuit.

Figure 7:
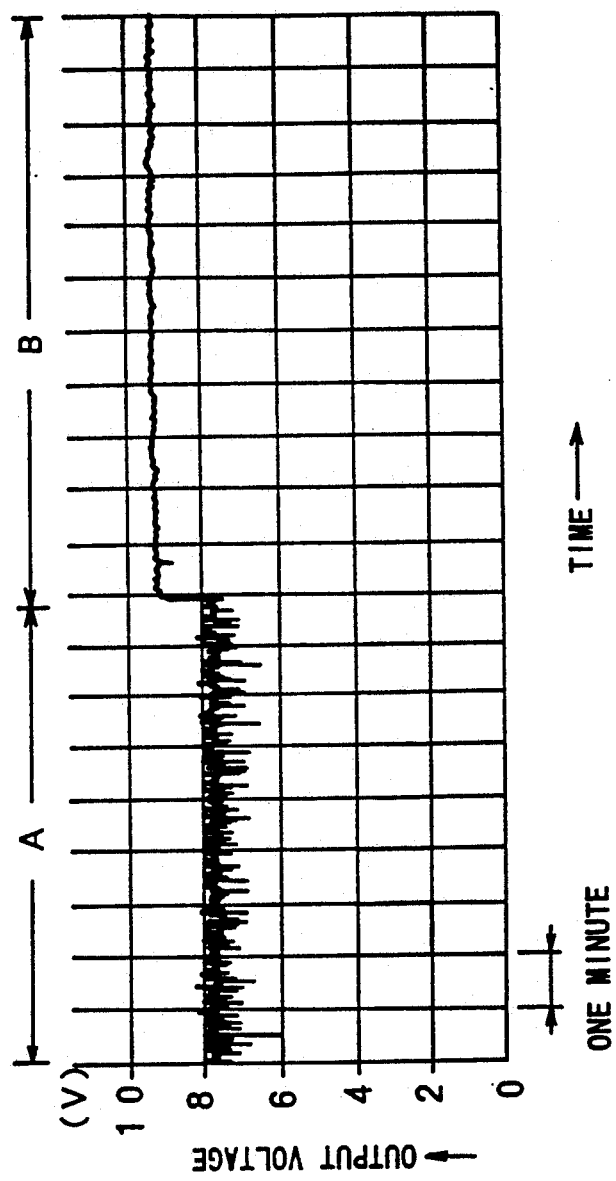
FIG. 7 is a graph showing an experimental result on the output voltage of the coagulation detecting circuit.

FIG. 7 is a graph showing the experimental results on the output voltage of the coagulation detecting circuit 65, in which the axis of abscissa represents time and the axis of ordinate represents an output voltage. Referring to FIG. 7, the mixed phase is in the normal state in a period A. In the normal state, since the mixed phase of the gas and powder is formed and fluidized, the output voltage represents a high-frequency variation. In contrast to this, when a coagulation is produced to attached on the inner wall surface of the reactor 10, the level of the output voltage is increased from the normal level by about 1.2 V, as in a period B, and no high-frequency variation occurs. In this manner, the state of the coagulation can be detected by monitoring the change in level of the output voltage and the presence of the high-frequency variation.

Figure 8:
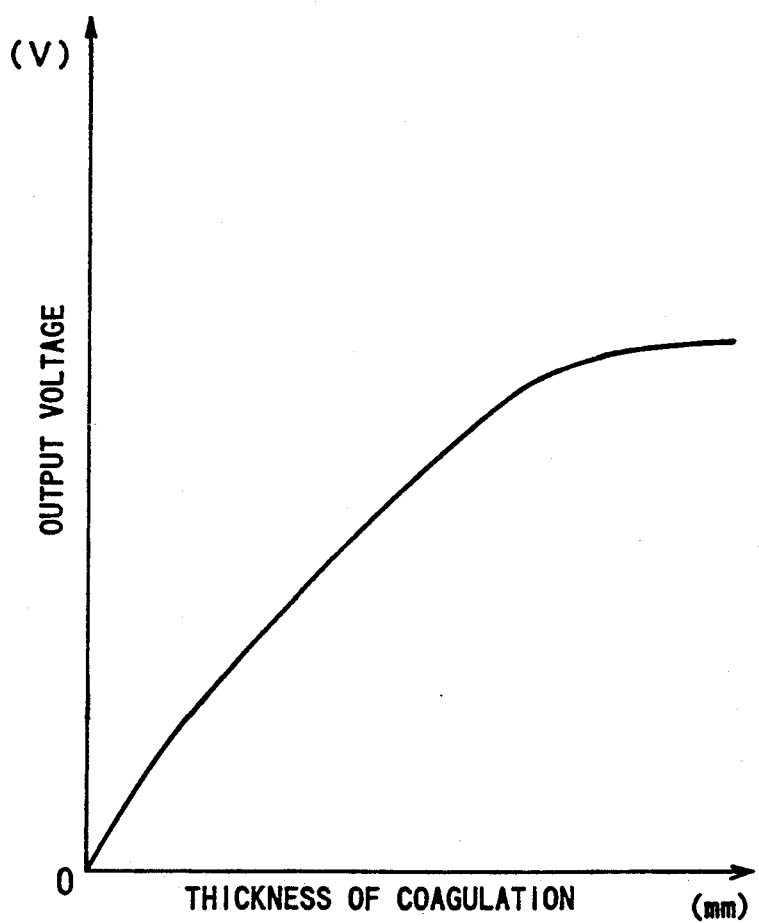
FIG. 8 is a graph showing a relationship between the thickness of coagulation and the output voltage of the coagulation detecting circuit.

In this experiment, since the coagulation having a certain thickness is forcibly attached at the final point of the period A, the voltage level is abruptly changed between the periods A and B. However, as shown in FIG. 8, in fact, the voltage level is gradually changed as the coagulation is attached and grown, and the thickness of the coagulation can be detected from the change in voltage level.

In this experiment, the coagulation detecting part 50 had a diameter of 4 B. The maximum size of the coagulation that can be detected by this coagulation detecting part 50 is about a diameter of 100 mm and a thickness of 50 mm. The detection area can be increased by increasing the diameter of the electrode, but the device becomes expensive. Hence, it is preferable to arrange a plurality of coagulation detecting parts 50 around the fluidized bed type olefin polymerization reactor 10. In this embodiment, eight coagulation detecting parts 50 are arranged in the vicinity of the dispersion plate 11 at the lower portion of the shell 10a (of which only two coagulation detecting parts 50 are illustrated in FIG. 2). It is preferable that the coagulation detecting part 50 is mounted about 100 mm above the dispersion plate 11 on which the coagulation 40 is apt to be formed and deposited. If the coagulation detecting part 50 projects into the reactor 10, fluidization of the mixed phase is disturbed. Therefore, it is preferable that the coagulation detecting part 50 is positioned so as not to project into the reactor 10. In this embodiment, the coagulation detecting part 50 are mounted such that its detection surface is flush with the inner wall surface of the reactor 10.

Figure 9:
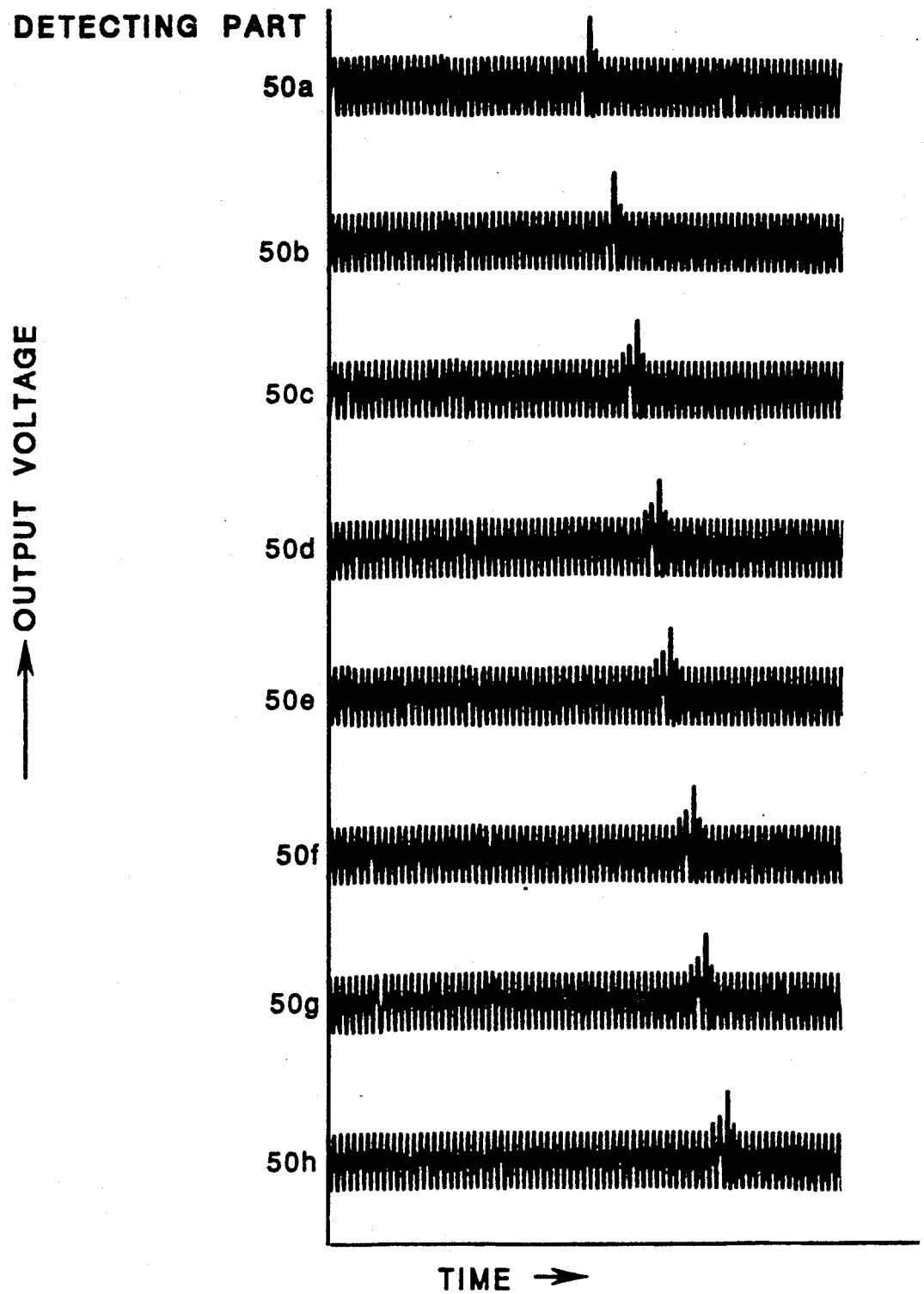
FIG. 9 shows output signals obtained by respective coagulation detecting parts mounted on the reactor.

The coagulation detecting part 50 can detect not only a coagulation 40 deposited on the inner wall surface of the reactor 10 but also a coagulation rolling on the inner wall surface. FIG. 9 shows output signals obtained by respective coagulation detecting parts 50a to 50f mounted on the reactor 10 in circumferentially spaced relationship to one another. Especially high-level signals can be seen in FIG. 9. On the basis of these high-level signals, it is recognized that a coagulation passes over the coagulation detecting parts 50a to 50f. Referring to FIG. 9, these high-level signals sequentially appear. This shows that a coagulation has rolled on the inner circumferential surface of the reactor 10 in the circumferential direction.

Figure 10:
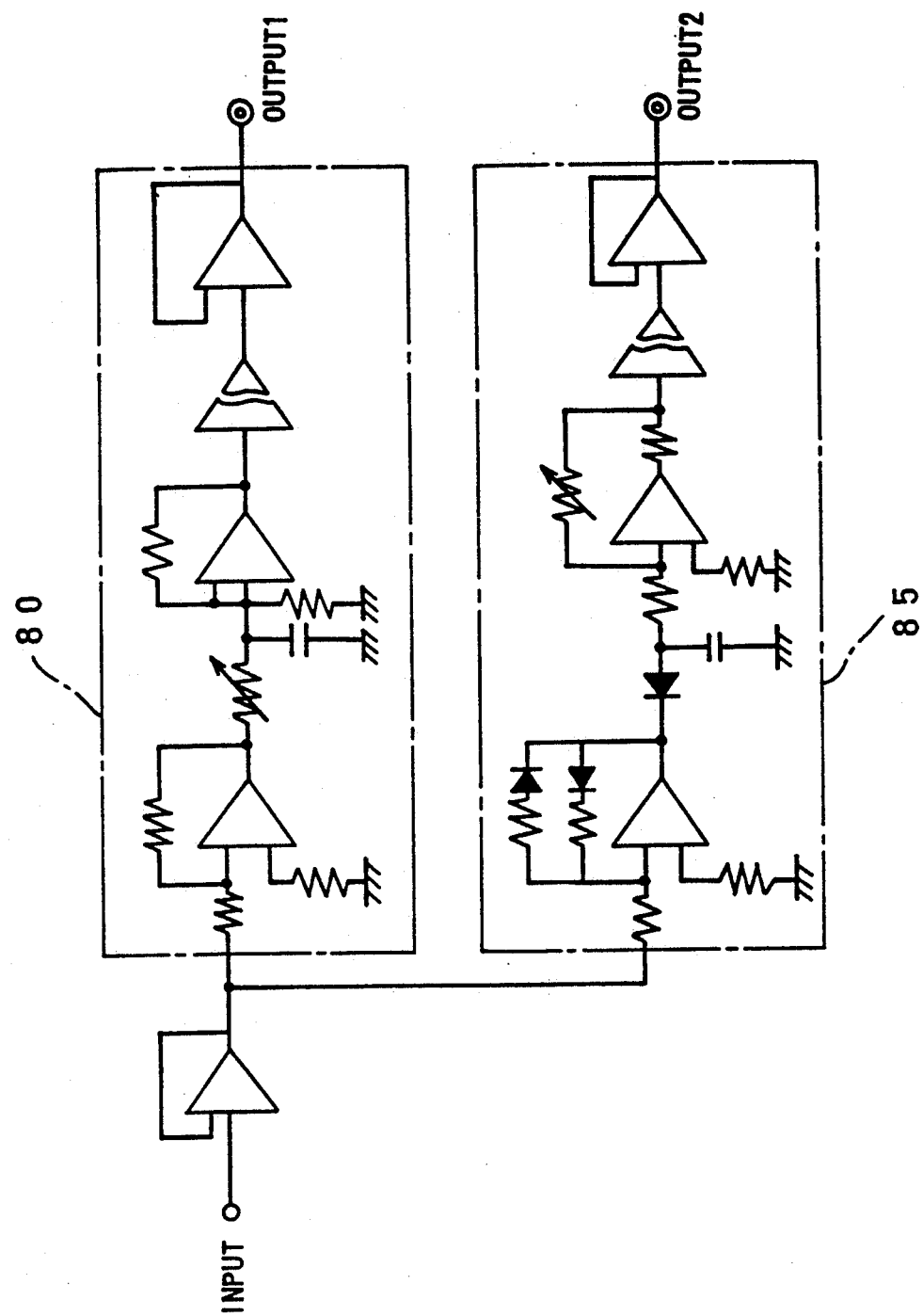
FIG. 10 shows another signal processing circuit having a circuit for outputting an average value and a circuit for detecting a change in amplitude.
Figure 11:
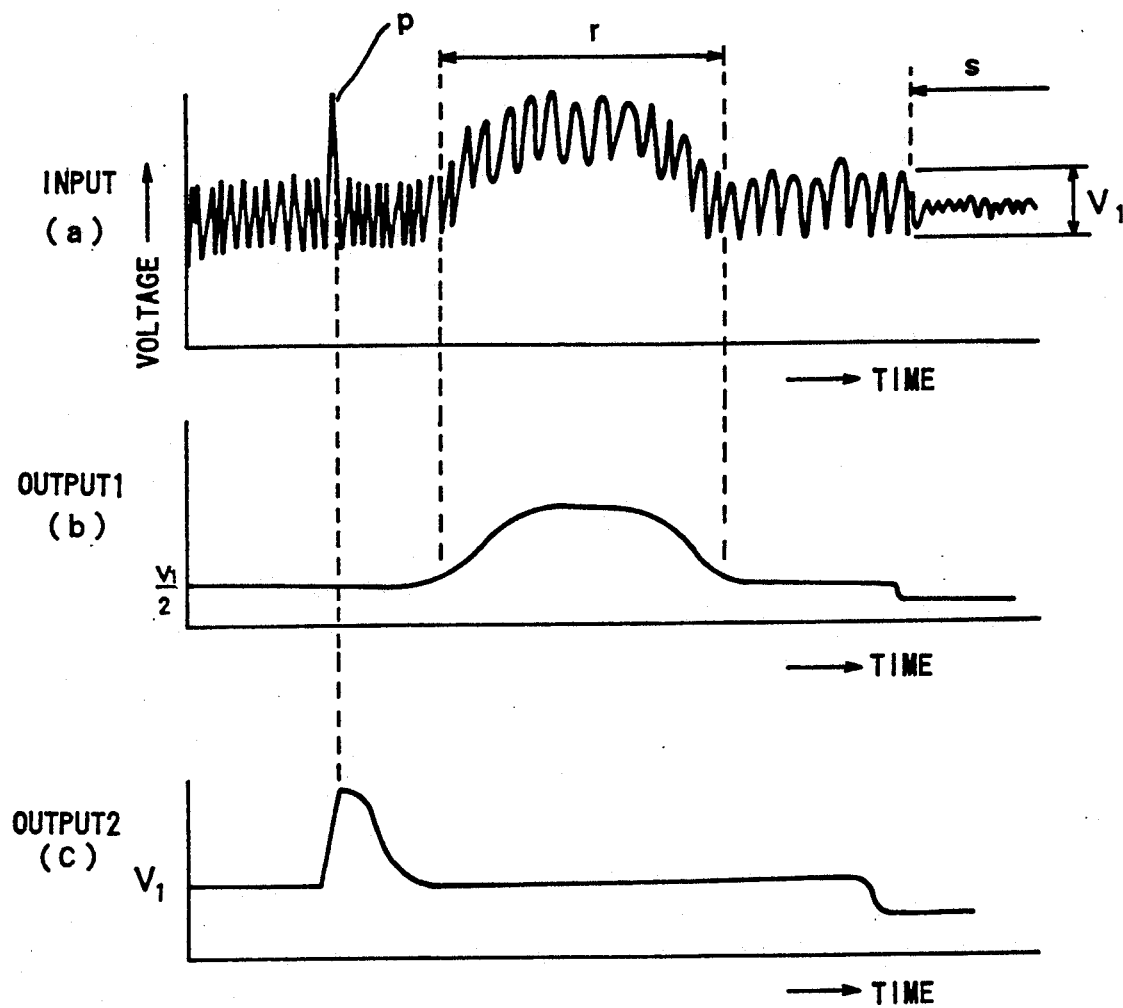
FIG. 11 shows signals processed by the signal processing circuit of FIG. 10.

A signal output from the signal processing circuit 60 is sent to the recording and/or alarming unit 70 through the cable 77 and monitored there. A signal output from the signal processing circuit 60 may be processed by various types of signal processing circuits, before it is directly input to the recording and/or alarming unit 70. FIG. 10 shows a second signal processing circuit having a circuit 80 for outputting an average value and a circuit 85 for detecting a change in amplitude. When a voltage signal as shown in FIG. 11(a), into which the output current signal from the first signal processing circuit 60 is converted, is input to this second signal processing circuit, the output signal from the average output circuit 80 has a waveform as shown in FIG. 11(b). FIG. 11(c) shows an output signal from the amplitude change detecting circuit 85. As is apparent from FIGS. 11(a) to 11(c), the average output circuit 80 does not output a signal (point P in FIG. 11(a)) corresponding to a moving coagulation, while the amplitude change detecting circuit 85 clearly outputs this signal. In a period r, a large amount of coagulation passes in front of the coagulation detecting part 50. Although this state cannot be recognized from the signal from the amplitude change detecting circuit 85, it appears in the signal from the average output circuit 80. In a period S, the state indicates that a coagulation starts to be attached on the reactor inner surface. The recording and/or alarming unit 70 can automatically produce an alarm on the basis of such a difference between the output signals.

Figure 12:
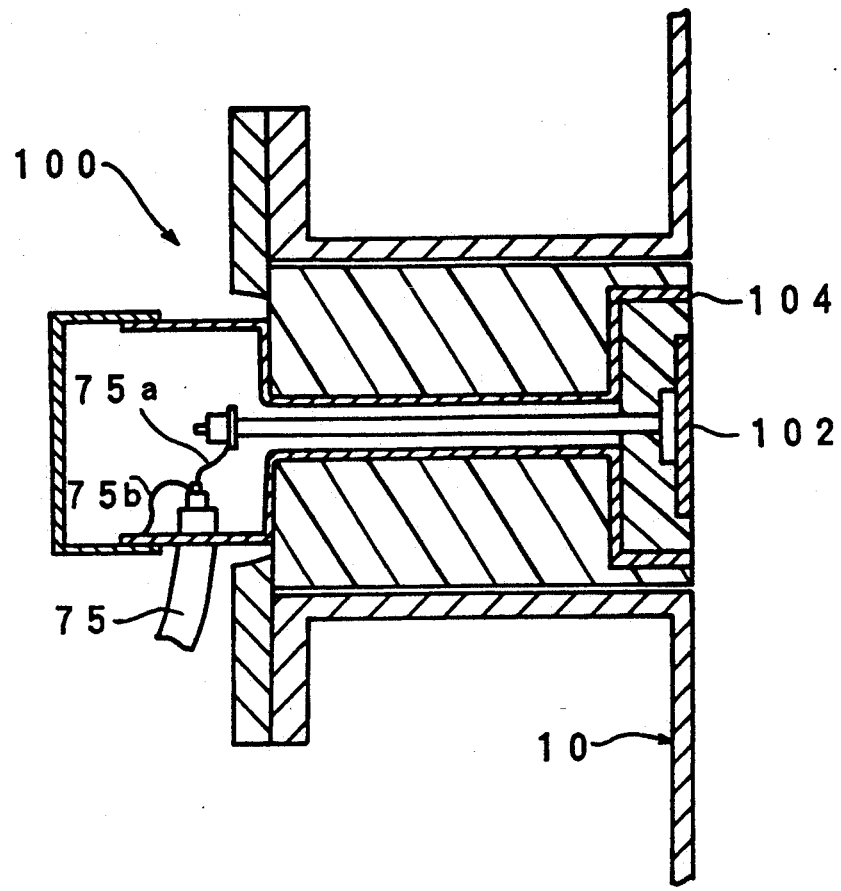
FIG. 12 is a view similar to that of FIG. 3 and shows a sectional view of a coagulation detecting part according to another embodiment of the present invention.
Figure 13:
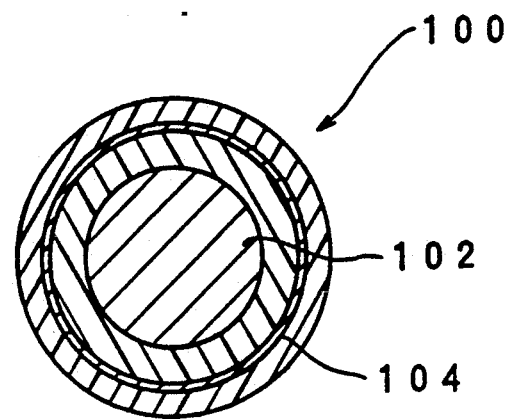
FIG. 13 is an end face view of the coagulation detecting part of FIG. 12.

FIGS. 12 and 13 show a construction of a coagulation detecting part 100 according to another embodiment of the present invention, in which FIG. 12 is a sectional view of the coagulation detecting part 100, and FIG. 13 is an end face view of the same. The coagulation detecting part 100 has a main electrode consisting of a single disk-like electrode plate 102, and a sub-electrode consisting of an annular electrode plate 104 coaxially surrounding the electrode plate 102. Although this coagulation detecting part 100 is different from the above-mentioned coagulation detecting part 50 in the number of electrode plates, its operation is substantially the same as that of the detecting part 50.

A means for detecting coagulations formed on the dispersion plate 11 will be described. A coagulation detecting device used in this case is substantially the same as that used for detecting the coagulation attached on the inner wall surface of the reactor 10 described above. The coagulation detecting device for detecting coagulations formed on the dispersion plate 11 has a coagulation detecting part, a coagulation detecting circuit connected to the coagulation detecting part, a signal processing circuit and a recording and/or alarming unit. The coagulation detecting circuit, the signal processing circuit and the recording and/or alarming unit are identical to those described above, and a detailed description thereof will be omitted.

Figure 14:
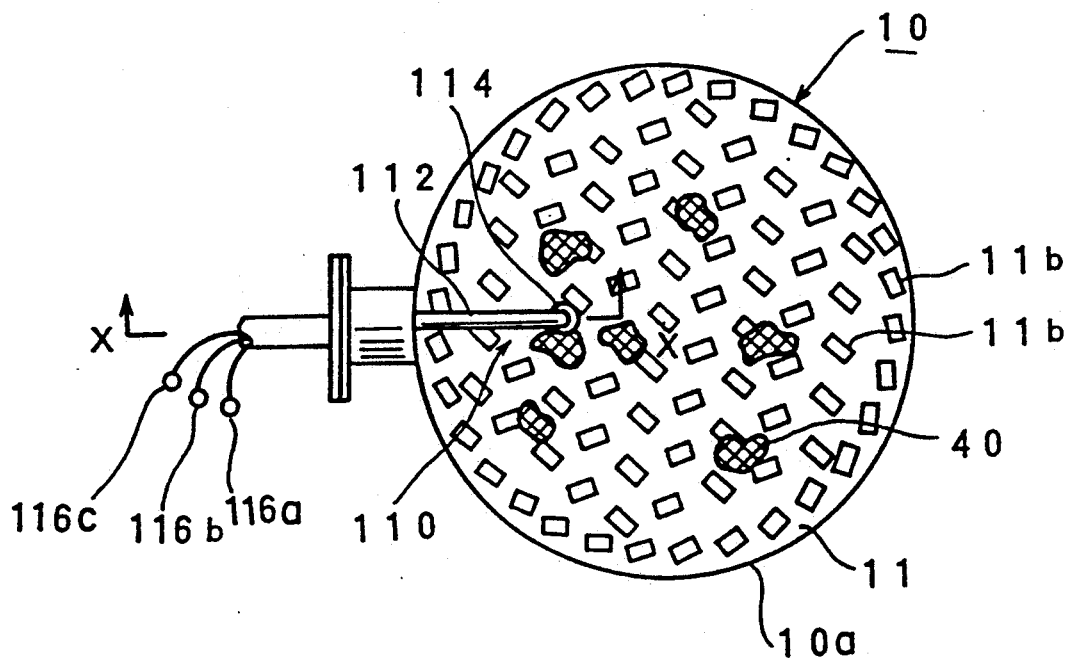
FIG. 14 is a cross-sectional view of a reactor on which a coagulation detecting part according to the third embodiment is mounted.
Figure 15:
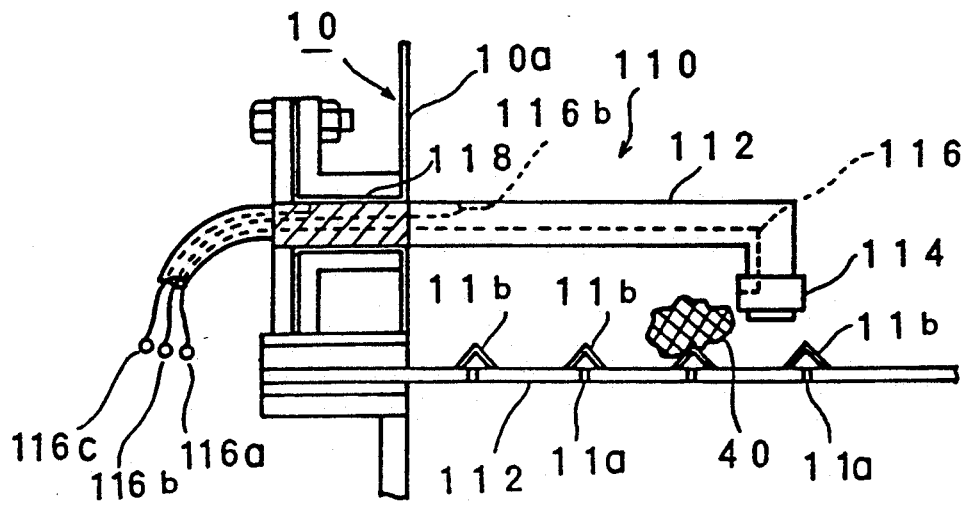
FIG. 15 is a sectional view taken along line x—x of FIG. 14.

FIG. 14 is a diagrammatic cross-sectional view of a shell 10a of a fluidized bed type olefin polymerization reactor 10, showing a coagulation detecting part 110 mounted thereon. FIG. 14 shows a dispersion plate 11 and the coagulation detecting part 110 when seen from the above. FIG. 15 is a sectional view taken along the line X—X of FIG. 14. The coagulation detecting part 110 has an arm-like tubular sub-electrode 112 extending toward the central portion of the reactor 10 through the shell 10a thereof. The distal end of the arm of sub-electrode 112 is bent downward, and a cylindrical main electrode 114 is mounted on the outer circumferential surface of the downward end portion of the electrode 112. The main electrode 114 is preferably positioned about 100 mm above the dispersion plate 11.

The main electrode 114 is connected to a lead wire 116a disposed in the sub-electrode 112, and a lead wire 116b is connected to the sub-electrode 112. A ground electrode 118 is electrically connected to the grounded shell 10a of the reactor 10 and the dispersion plate 11. The ground electrode 118 is connected to a lead wire 116c. The lead wires 116a to 116c are respectively connected to terminals $E_1$, $E_2$ and $E_3$ of the above-mentioned circuit shown in FIG. 6. Hence, when a coagulation 40 approaches an area between the main electrode 114 and the dispersion plate 11, a change in capacitance is monitored, thereby detecting the coagulation 40. Also, not only a coagulation 40 passing through a portion immediately under the main electrode 114 but also a coagulation 40 passing through a portion relatively remote from the main electrode 114 can be detected because of the presence of the sub-electrode 112.

The coagulations 40 formed on the dispersion plate 11 are not fixed, but are moved by a change in fluidization of the mixed phase or by a change in fluidization caused by periodical discharge of the product from the reactor 10. Hence, any coagulation 40 on the dispersion plate 11 will pass through the vicinity of the main electrode 114 sooner or later and thus will be detected. When the size and number of the coagulations 40 are increased, the probability that the coagulations 40 pass through the vicinity of the main electrode 114 is increased. Therefore, even a single coagulation detecting part 110 can sufficiently detect the coagulations. However, if a plurality of coagulation detecting parts 110 are arranged, the detection probability can be further increased.

Note that a roof 11b having two open side surface portions is provided on each of a multiple of openings 11a formed in the dispersion plate 11. Hence, a direct upward blow of the circulation gas supplied upward from the bottom head 10b of the reactor 10 through the dispersion plate 11 is blocked by the roofs 11b, and the flowing force is dispersed. This aims at obtaining a preferable fluidized state of the mixed phase.

In the same manner as in the case of the above-mentioned coagulation detecting part 50, a change in capacitance of the coagulation detecting part 110 is converted to an electrical signal by a coagulation detecting circuit (not shown), and then the electrical signal is converted to a current signal of 4 to 20 mA by a signal processing circuit (not shown) which is in turn transferred to a recording and/or alarming unit (not shown).

Figure 16:
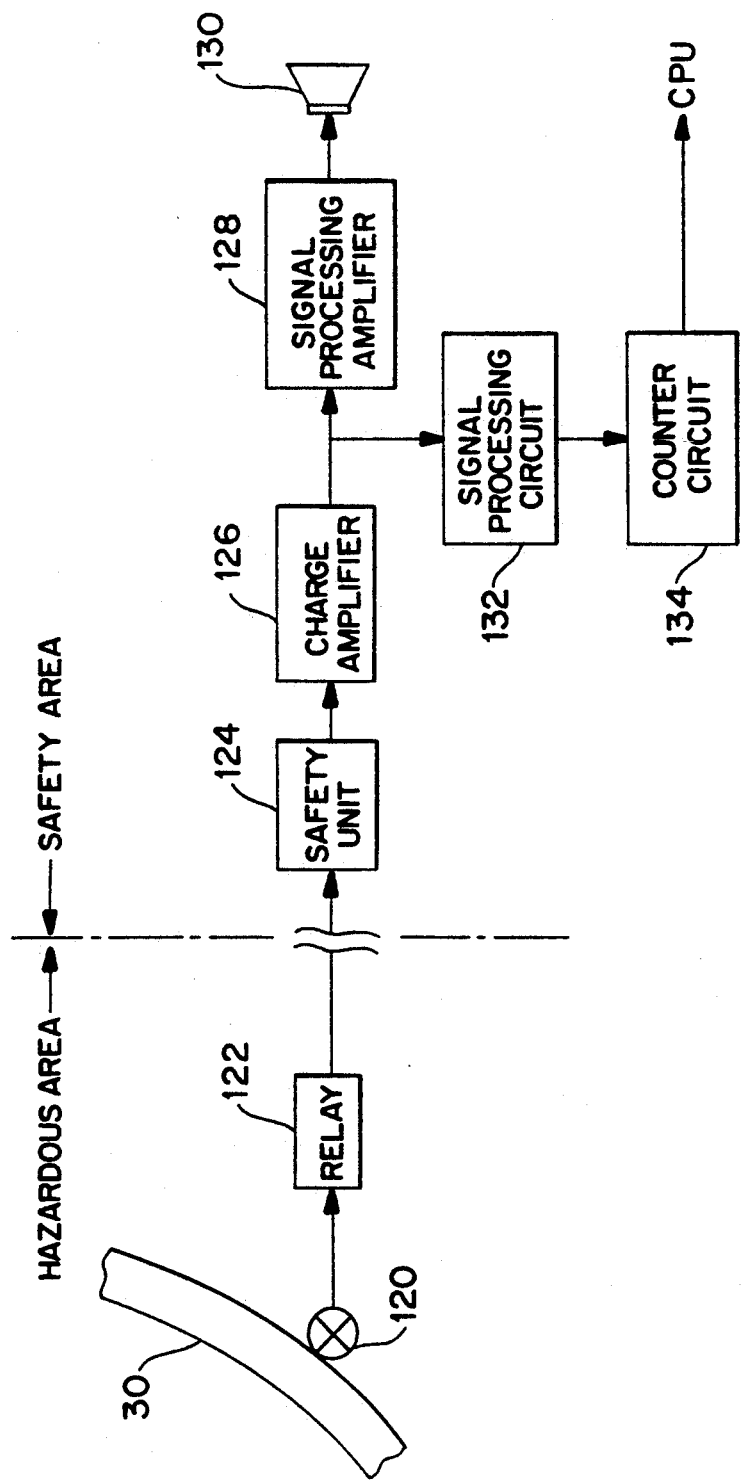
FIG. 16 shows a bent portion of the pneumatic line of FIG. 1 on which a vibration sensor as a coagulation detecting part are mounted and its associated signal processing circuits.

A means for detecting a coagulation in a product discharge pipe will be described. FIG. 16 shows a bent portion of the pneumatic line 30 shown in FIG. 1. A vibration sensor 120 is mounted at the bent portion of the pneumatic line 30. The vibration sensor 120 serves to convert vibration noise, produced when a coagulation transported through the pneumatic line 30 impinges against the pneumatic line 30, into an electrical signal. Accordingly, the vibration sensor 120 is preferably mounted at a bent portion, as shown in FIG. 16. A piezoelectric element or the like may be used as the vibration sensor 120. An output signal from the vibration sensor 120 is supplied to a charge amplifier 126 through a relay box 122 and a safety unit 124. An output from the charge amplifier 126 is filtered by a signal processing amplifier 128 and transmitted to two systems, i.e. one system for operating a loudspeaker 130, and another system for performing filtering and sampling peaks having an amplitude exceeding a predetermined value by a signal processing circuit 132 and for counting the number of peaks by a counter circuit 134.

In the counting system, data output from the counter circuit 134 is sent to a data processing unit (not shown) to be subjected to appropriate analysis. Filtering by the signal processing amplifier 128 and the signal processing circuit 132 is performed by using a band-pass filter having a range of 2 to 4 kHz or the like. Sampling by the signal processing circuit 132 is performed for wave-shaping the signal with a predetermined threshold value. The line from the vibration sensor 120 to the relay box 122 is installed at a so-called hazardous area in the vicinity of the product discharge pipe, and the line including the respective circuits following the safety unit 124 is installed at a safety area remote from the product discharge pipe.

Figure 17:
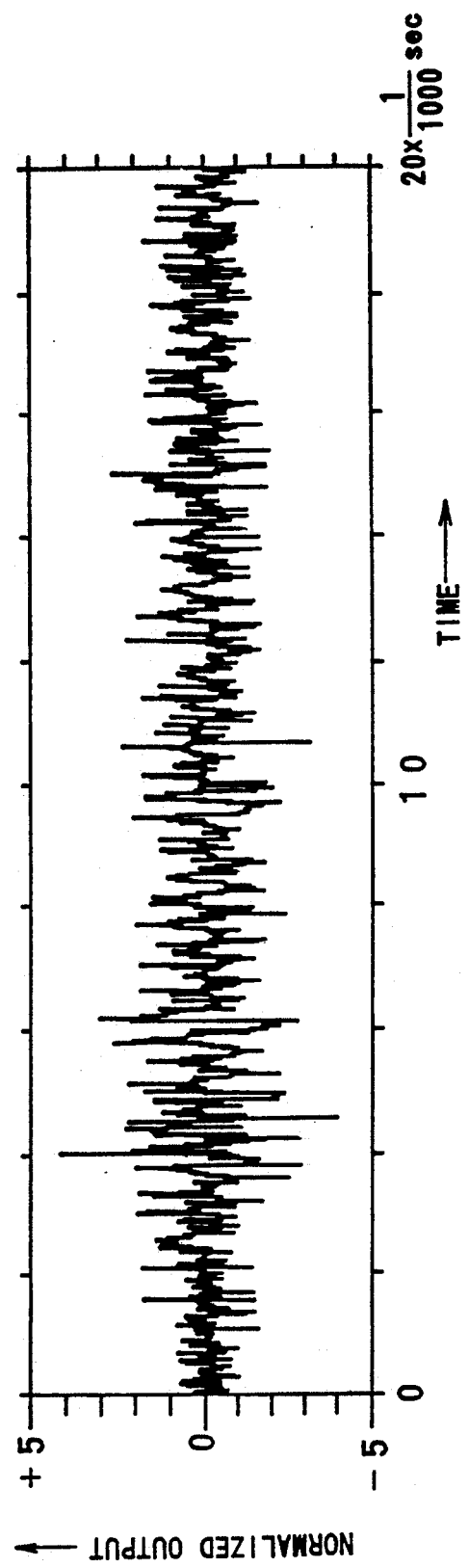
FIG. 17 shows a waveform of a signal output from a charge amplifier among the circuit shown in FIG. 16.
Figure 18:
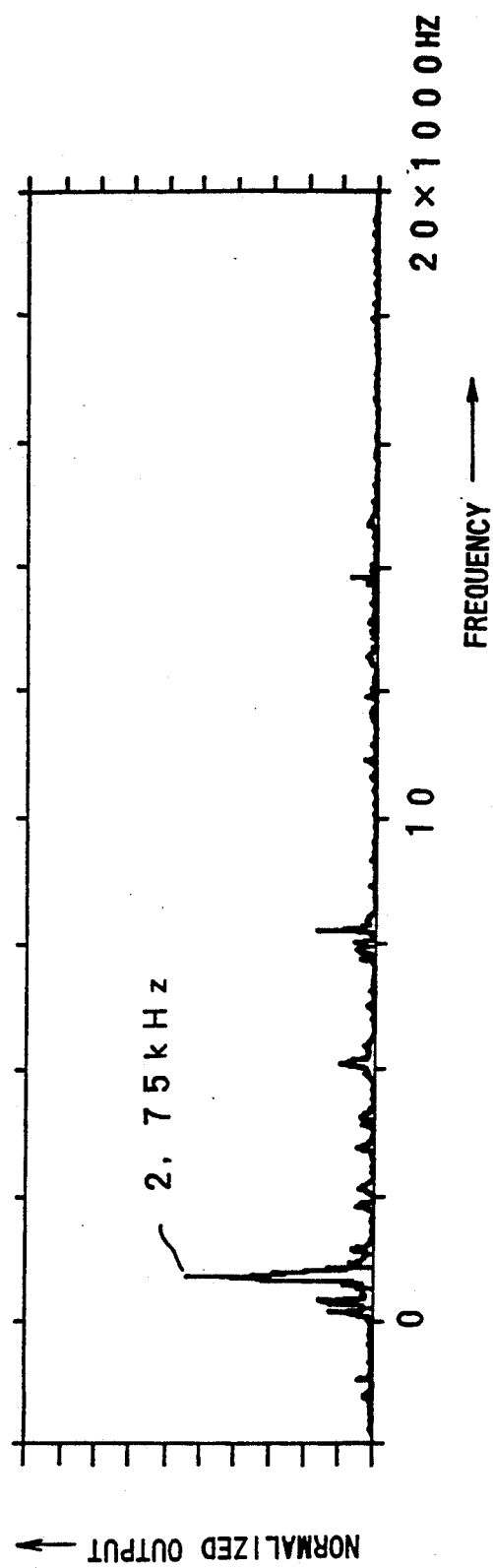
FIG. 18 is a graph obtained by frequency-analyzing the waveform of the signal output from the charge amplifier.

FIG. 17 shows an output waveform of the charge amplifier 126 before signal-processing, e.g., filtering, in which the axis of abscissa represents time, and the axis of ordinate represents a normalized output. FIG. 18 is a graph obtained by frequency-analyzing the waveform of the output from the charge amplifier 126, in which the axis of abscissa represents the frequency, and the axis of ordinate represents a normalized output. As is apparent from FIG. 18, a peak exists at a frequency of 2.75 kHz in this example. More specifically, it was clarified by an experiment that the peak present in the vicinity of 2.75 kHz indicated the frequency and output value of noise produced when a coagulation impinged against the pipe. Hence, in order to detect a coagulation in the product discharge pipe (pneumatic line 30) of this fluidized bed type olefin polymerization reactor 10, a filter for passing only a frequency in the 2- to 4-kHz band and a threshold circuit may be incorporated in the signal processing circuit 132, and a signal exceeding a preset threshold value may be counted by the counter circuit 134.

The correlation between the output value and the size of the coagulation can be easily obtained by collecting the coagulation and comparing it with the output value. When the correlation between the output and the coagulation is obtained and the threshold value is set at a desired value, the number of coagulations in the product discharge pipe (pneumatic line 30) can be counted.

In this manner, the coagulation forming state in the reactor 10 can be estimated by detecting the number of coagulations in the product discharge pipe. Also, clogging of the product discharge line (pneumatic line 30) can be prevented.

With regard to the system for operating the loudspeaker 130, if the loudspeaker 130 is arranged in a monitor room, the operator in the monitor room can hear the noise produced by coagulations flowing in the discharge pipe. If the operator has a knowledge on the relationship between the coagulations and flowing noise, he can know a change in coagulation state in the discharge pipe on the basis of the change in noise.

All the embodiments described above relate to a fluidized bed type olefin polymerization reactor. However, the present invention is not limited to it, and can be applied to a container and pipes for a mixed phase of a powder and a gas. For example, the present invention can be applied to a fluidized bed dryer, a slurry tank, a slurry pipe, and the like.

As has been described above, according to the coagulation detecting device of the present invention, the coagulation state in the mixed phase container can be detected from a change in capacitance or a change in vibration noise in the discharge pipe depending on formation of coagulations. The coagulation detecting device of the present invention is considerably safe compared to the conventional devices using radiation. Furthermore, in the coagulation detecting device of the present invention using the capacitance sensing means, the precision in coagulation detection can be improved by appropriately selecting the shape and the number of coagulation detecting part.

It is thought that the present invention and many of its attendant advantages will be understood from the foregoing description and it will be apparent that various changes may be made in the form, construction and arrangement thereof without departing from the spirit and scope of the invention or sacrificing all of its material advantages, the form hereinbefore described being merely a preferred or exemplary embodiment thereof.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

We claim:

1. A coagulation detecting device for detecting a coagulation in a reactor area of a mixed phase container in which a mixed phase of a gas and a powder is formed and fluidized, said device comprising:

a coagulation detecting part comprising an electrode adapted to be mounted on a conductive inner wall surface of said mixed phase container which defines a portion of said reactor area, whereby a capacitance is introduced between said electrode and a surrounding portion of said inner wall surface which surrounds said electrode, and a terminal adapted to be electrically connected to said surrounding portion; and a coagulation detecting circuit for outputting an electrical signal in correspondence to the capacitance between said electrode and said surrounding portion, whereby a coagulation can be detected from a change in electrical signal output therefrom, said coagulation detecting circuit being electrically connected to said coagulation detecting part.

2. A device according to claim 1, wherein said coagulation detecting circuit comprises a bridge circuit comprised of a first AC power supply, a second AC power supply, a first capacitor and a second capacitor connected in series to form a rectangle, a terminal of said first AC power supply being connected to a terminal of said second AC power supply, said electrode of said coagulation detecting part being connected to a junction between said first AC power supply and said first capacitor, and said terminal of said coagulation detecting part being connected to a junction between said first and second capacitors.

3. A device according to claim 2, wherein said coagulation detecting part further comprises a sub-electrode adapted to be positioned between said electrode and said surrounding portion of said coagulation detecting part and connected to a junction between said first and second AC power supplies of said bridge circuit.

4. A device according to claim 1, wherein a plurality of said coagulation detecting parts are disposed in said inner wall surface of said mixed phase container at predetermined intervals in a circumferential direction.

5. A device according to claim 3, wherein said electrode of said coagulation detecting part comprises a disk-like electrode plate, and said sub-electrode comprises an annular electrode plate disposed around said disk-like electrode plate at a predetermined spacing.

6. A device according to claim 1, further comprising means for recording the signal output from said coagulation detecting circuit.

7. A device according to claim 1, further comprising means for producing an alarm on the basis of the signal from said coagulation detecting circuit.

8. A device according to claim 1, wherein said mixed phase container is a fluidized bed, olefin polymerization reactor.

9. A coagulation detecting device for detecting a coagulation in a reactor area of a mixed phase container in which a mixed phase of a gas and a powder is formed and fluidized, said mixed phase container having a conductive dispersion plate which defines a bottom portion of said reactor area, said device comprising:

a coagulation detecting part comprising (a) an arm adapted to be mounted on a side wall of said mixed phase container above said dispersion plate, said arm extending from said side wall toward the central portion of said mixed phase container and having a distal end portion bent downward, (b) an electrode mounted on said distal end portion of said arm, whereby a capacitance is introduced between said electrode and said dispersion plate, and (c) a terminal adapted to be electrically connected to said dispersion plate; and a coagulation detecting circuit for outputting an electrical signal in correspondence to the capacitance between said electrode and said dispersion plate, whereby a coagulation can be detected from a change in electrical signal output therefrom, said coagulation detecting circuit being electrically connected to said electrode and said terminal of said coagulation detecting part.

10. A device according to claim 9, wherein said coagulation detecting circuit comprises a bridge circuit comprised of a first AC power supply, a second AC power supply, a first capacitor and a second capacitor connected in series to form a rectangle, a terminal of said first AC power supply being connected to a terminal of said second AC power supply, said electrode of said coagulation detecting part being connected to a junction between said first AC power supply and said first capacitor, and said terminal of said coagulation detecting part being connected to a junction between said first and second capacitors.

11. A device according to claim 10, wherein said coagulation detecting part further comprises a sub-electrode being electrically insulated from said electrode of said coagulation detecting part and connected to a junction between said first and second AC power supplies of said bridge circuit.

12. A device according to claim 9, further comprising means for recording the signal output from said coagulation detecting circuit.

13. A device according to claim 9, further comprising means for producing an alarm on the basis of the signal from said coagulation detecting circuit.

14. A device according to claim 9, wherein said mixed phase container is a fluidized bed, olefin polymerization reactor.

* * * * *